(12) United States Patent
Yamakawa et al.

(10) Patent No.: US 8,677,192 B2
(45) Date of Patent: Mar. 18, 2014

(54) INFORMATION CORRECTION SUPPORT SYSTEM AND METHOD

(75) Inventors: Kazuo Yamakawa, Takamatsu (JP); Koichi Hiramoto, Kawasaki (JP); Isao Sumito, Takamatsu (JP); Kazuma Takahashi, Takamatsu (JP); Naoto Hamada, Takamatsu (JP); Hitoshi Kamura, Takamatsu (JP)

(73) Assignee: Fujitsu Limited, Kawasaki (JP)

( * ) Notice: Subject to any disclaimer, the term of this patent is extended or adjusted under 35 U.S.C. 154(b) by 405 days.

(21) Appl. No.: 13/047,483

(22) Filed: Mar. 14, 2011

(65) Prior Publication Data

US 2012/0066540 A1 Mar. 15, 2012

(30) Foreign Application Priority Data

Mar. 26, 2010 (JP) .................................. 2010-72127

(51) Int. Cl.
*G06F 11/00* (2006.01)
(52) U.S. Cl.
USPC ............................................. 714/48; 714/49
(58) Field of Classification Search
USPC .................................................... 714/48, 49
See application file for complete search history.

(56) References Cited

U.S. PATENT DOCUMENTS

| | | | |
|---|---|---|---|
| 6,925,599 B2 * | 8/2005 | Wood | 715/229 |
| 2002/0035570 A1 * | 3/2002 | Kozam et al. | 707/104.1 |
| 2008/0270420 A1 * | 10/2008 | Rosenberg | 707/10 |
| 2009/0083703 A1 * | 3/2009 | Grady et al. | 717/109 |
| 2011/0218980 A1 * | 9/2011 | Assadi | 707/700 |
| 2011/0261194 A1 * | 10/2011 | Udani | 348/135 |

FOREIGN PATENT DOCUMENTS

| | | |
|---|---|---|
| JP | 11-31041 | 2/1999 |
| JP | 2004-220599 | 8/2004 |
| JP | 2006-323486 | 11/2006 |

* cited by examiner

*Primary Examiner* — Philip Guyton
(74) *Attorney, Agent, or Firm* — Fujitsu Patent Center (57) ABSTRACT

An information correction support system includes a first information providing unit to provide first information that is input by a first user to a second user, a first information accepting unit to accept an error entry position in the first information and second information that is correct information for the input error entry that are input by the second user, an error entry position providing unit to provide the accepted error entry position to the first user without providing the accepted second information, a second information accepting unit to accept third information that is correction information for the error entry input by the first user, a correctness determination unit to determine whether the accepted third information is correctly input information based on the accepted second information, and a warning unit to warn the first user according to a determination by the correctness determination unit.

10 Claims, 12 Drawing Sheets

| | A | B | C | D | E | F | G | H |
|---|---|---|---|---|---|---|---|---|
| 1 | ◆OFF LINE SDV CHECK SHEET ◆ | | | | | | | |
| 2 | | | | | | | | |
| 3 | | ■ SEARCH CRITERIA | | | | | | |
| 4 | | SUBJECT NUMBER | :h-00001 | | | | | |
| 5 | | CASE NUMBER | :0001-001 | | | | | |
| 6 | | CLINICAL TRIAL FACILITY | :AAA HOSPITAL | | | | | |
| 7 | | PHYSICIAN IN CHARGE OF CLINICAL TRIAL | :XXXX HANAKO | | | | | |
| 8 | | SDV ENVIRONMENT | :OFF LINE | | | | | |
| 9 | | VISIT | :ONE WEEK AFTER ADMINISTERING DRUG | | | | | |
| 10 | | CRF SELECTION | :BLOOD PRESSURE AND BODY TEMPERATURE MEASUREMENT | | | | | |
| 11 | | | | | | | | |
| 12 | | | | | | | | |
| 13 | | ■ SEARCH CRITERIA | | | | | | |
| 14 | | | | | | | | |
| 15 | | CRF | ITEM | REGISTERED DATA | RESULT | OFF LINE SDV QUERY CONTENT | CORRECTION VALUE | |
| 16 | | | TIME AND DATE OF MEASUREMENT OF BLOOD PRESSURE AND BODY TEMPERATURE | 2009/6/1 12:12:12 | GOOD | | | |
| 17 | | | BODY TEMPERATURE | 36.4 | NO GOOD | VALUE IN crf DOES NOT MATCH WITH REGISTERED VALUE | 37.1 | |
| 18 | | | SYSTOLIC BLOOD PRESSURE | 100 | GOOD | | | |
| 19 | | | | 80 | GOOD | | | |
| 20 | | | | | | | | |

URL

REPLY

· PHYSICIAN'S NAME : XXXX HANAKO    · CURRENT TIME AND DATE : 2009/06/02 20:12:44

● SUBJECT NUMBER : h-000001           ● CASE NO. :              0001-001
● STATE:            ISSUED
● QUERY ID:         Q00000073          ● TYPE:                  MANUAL QUERY
● ISSUER:           EDC TEST ADMINISTRATOR
● QUERY CONTENT:   ITEM [BODY TEMPERATURE]   ● TIME AND DATE OF ISSUE:  2009/06/02 13:12:20
                   VALUE IN crf DOES NOT MATCH WITH REGISTERED VALUE

| VISIT | ONE WEEK AFTER ADMINISTERING DRUG |
|---|---|
| CRF | MEASUREMENT OF BLOOD PRESSURE AND BODY TEMPERATURE |
| ITEM | BODY TEMPERATURE |
| VALUE AT ISSUE (REGISTERED DATA) | 36.4 |
| VALUE BEFORE CORRECTION | 36.4 |

● VALUE AFTER CORRECTION         37.0         — TX21
● REASON FOR CORRECTION    INPUT MISTAKE/TRANSCRIPTION MISTAKE ▼  — MN21

BN21
                                              REPLY

INFORMATION CORRECTION SUPPORT SYSTEM AND METHOD

CROSS-REFERENCE TO RELATED APPLICATION

This application is based upon and claims the benefit of priority of the prior Japanese Patent Application No. 2010-072127, filed on Mar. 26, 2010, the entire contents of which are incorporated herein by reference.

FIELD

The embodiment discussed herein is related to an information correction support system.

BACKGROUND

A pharmaceutical company needs to conduct a clinical trial for a newly developed drug and apply for an approval by attaching a Case Report Form (CRF) that indicates the result of the clinical trial in order to obtain the approval by the government for manufacturing and distributing the newly developed drug (hereinafter described as "new drug").

A pharmaceutical company requests medical institutions such as hospitals to conduct a clinical trial. A physician who works for the medical institution that received the request conducts the clinical trial, creates CRFs to submit to the pharmaceutical company. Recently, Electronic Data Capture (EDC) systems have been used for capturing CRFs as electronic data, "electronic CRFs." Japanese Laid-open Patent Publication No. 2004-220599 discusses an example of an EDC.

The pharmaceutical company checks a CRF against the original document to determine whether any error entry exists. The check task is called Source Document Verification or Source Data Verification. Alternatively, the check task is simply called SDV.

An error entry in the CRF needs to be corrected by a physician. If the physician is informed about the error entry and a correct value by the pharmaceutical company, the physician can easily correct the error entry without referring to the original document.

However, the above-described correction method is not always preferable. This is because that a result of the SDV by the pharmaceutical company may be wrong. Moreover, the pharmaceutical company may inform an incorrect value with an intention or negligence even if the pharmaceutical company found an error entry in the CRF.

Accordingly, the physician needs to check the original document against the CRF and correct the CRF without being informed about a correct value from the pharmaceutical company. An amount of original documents is enormous, and the correction task is a heavy burden on the physician.

Accordingly, improving accuracies to create a CRF is considered. For example, a physician, an examination engineer, or a subject enters each item that makes up a form using an electronic pen. A server identifies original data entered in each item by the user, based on entry data acquired through the electronic pen. The server then compares the identified original data with essential data for creating the case report form and determines whether there is any omission in entry. When it is determined that there is an omission in entry, the server prepares a warning message to the effect and transmits the message to a terminal device which transmitted the entry data. When it is determined that there is no omission in entry, the server creates the case report form based on the identified original data (for example, Japanese Laid-open Patent Publication No. 2006-323486).

Moreover, a method to check correctness may be considered in which two operators input data for each item separately, and the input two units of data are compared (for example, Japanese Laid-open Patent Publication No. 11-31041).

In order to compare a CRF with the original data by a computer such as a server, the original data needs to be electronic data. However, a document that becomes original data, for example, a medical record is still written in a paper form.

Furthermore, according to the method in which each data is input by two operators, two physicians have to input a CRF. Thus, burdens on the physicians become significant. According to the method, a CRF may not be input correctly by only one physician.

SUMMARY

According to an aspect of the invention, a system configured to support in correcting input information includes a first information providing unit configured to provide first information that is input by a first user to a second user; a first information accepting unit configured to accept an error entry position in the first information and second information that is correct information for the error entry that are input by the second user; an error entry position providing unit configured to provide the error entry position accepted by the first information accepting unit to the first user without providing the second information accepted by the first information accepting unit; a second information accepting unit configured to accept third information that is correction information for the error entry input by the first user; a correctness determination unit configured to determine whether the third information accepted by the second information accepting unit is correctly input information based on the second information accepted by the first information accepting unit; and a warning unit configured to warn the first user when the correctness determination unit determines the third information is incorrectly input information.

The object and advantages of the invention will be realized and attained at least by the elements, features, and combinations particularly pointed out in the claims.

It is to be understood that both the foregoing general description and the following detailed description are exemplary and explanatory and are not restrictive of the invention, as claimed.

DESCRIPTION OF EMBODIMENT

Figure 1:
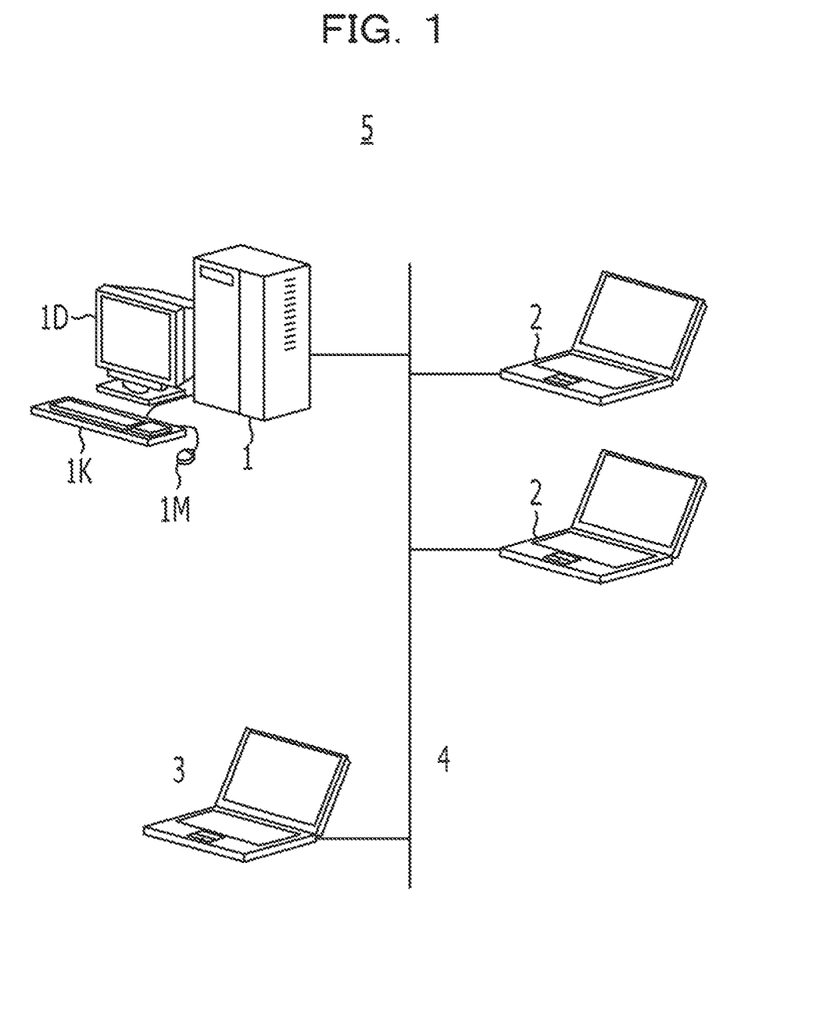
FIG. 1 illustrates an example of an overall configuration of a CRF correction support system.
Figure 2:
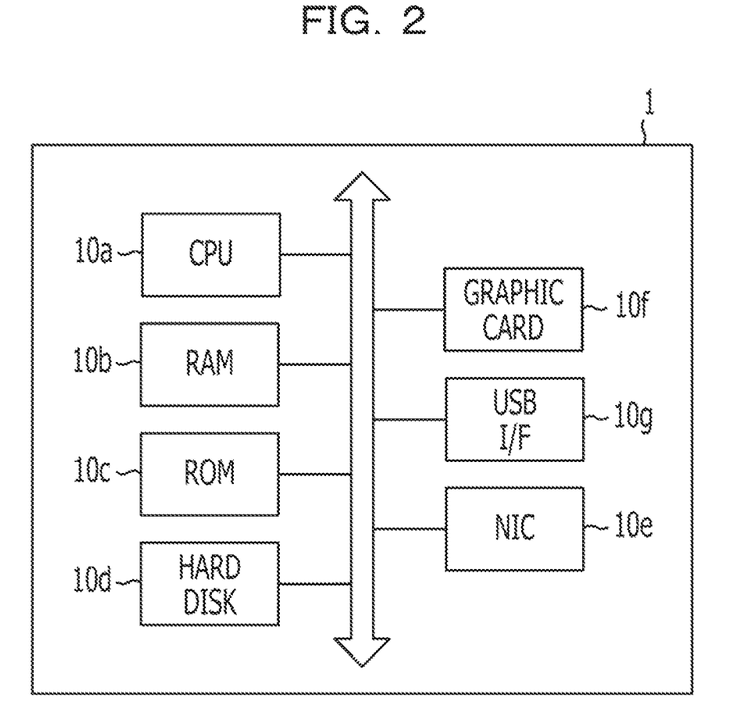
FIG. 2 illustrates an example of a hardware configuration of a CRF management server.
Figure 3:
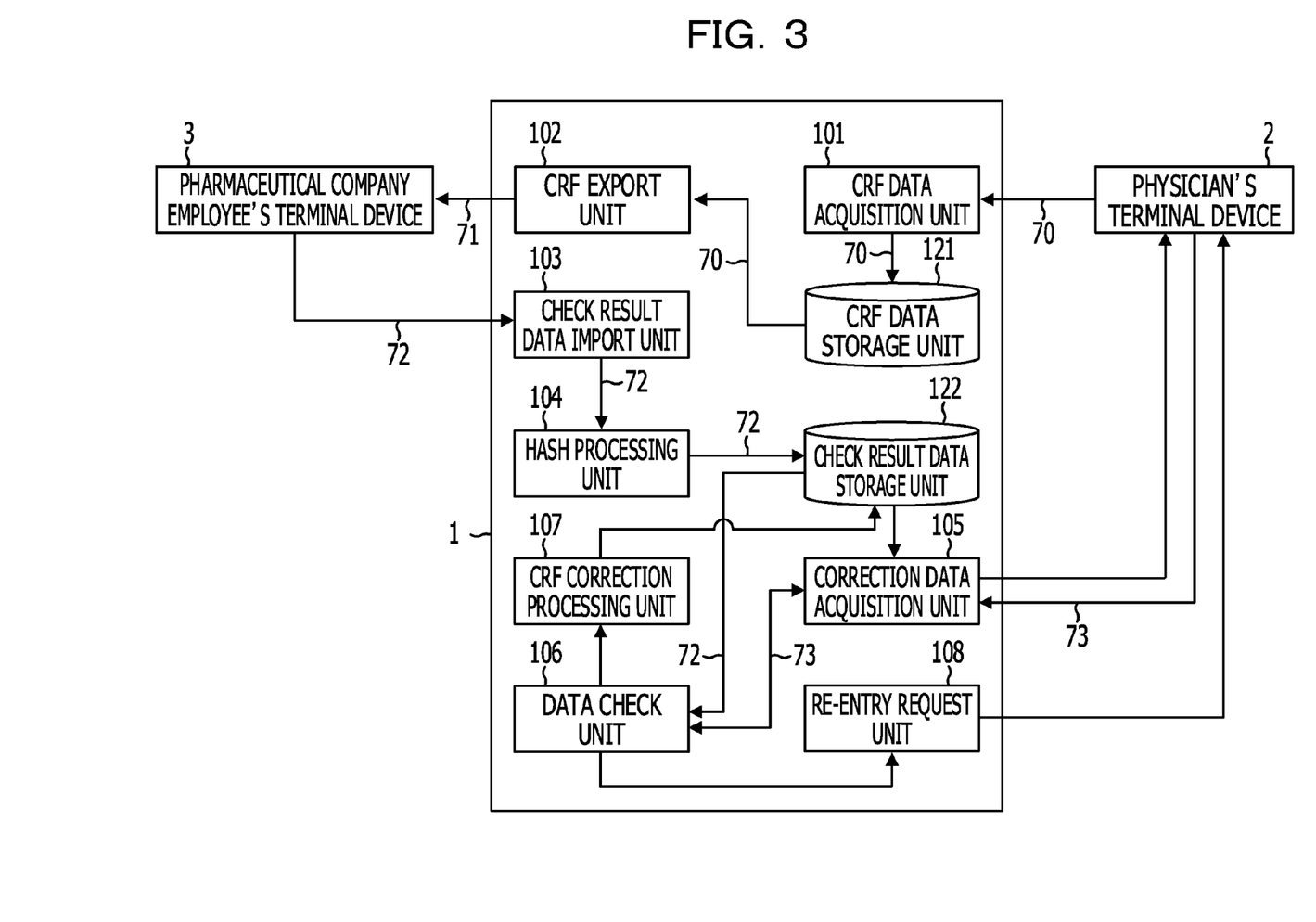
FIG. 3 illustrates an example of a functional configuration of the CRF management server.
Figure 4:
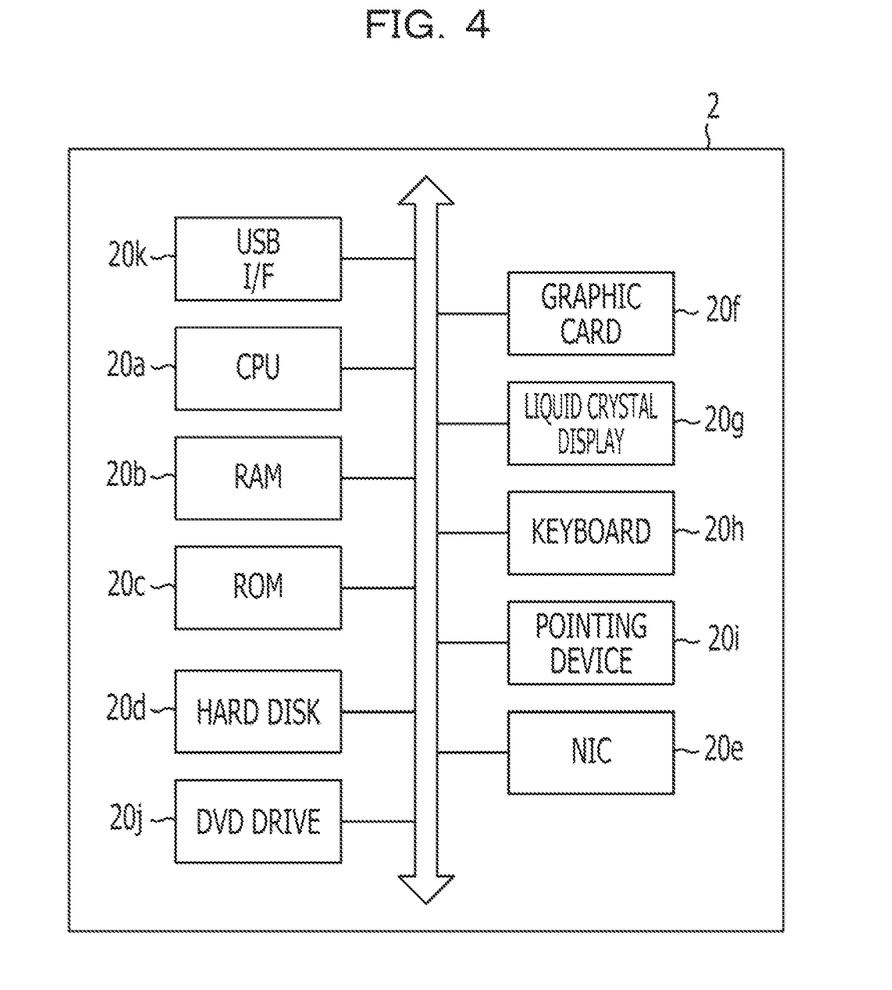
FIG. 4 illustrates an example of a hardware configuration of a physician's terminal device.

FIG. 1 illustrates an overall configuration of a CRF correction support system (information correction support system) 5. FIG. 2 illustrates an example of a hardware configuration of a CRF management server (server, information correction support server) 1. FIG. 3 illustrates an example of a functional configuration of the CRF management server 1. FIG. 4 illustrates an example of a hardware configuration of a physician's terminal device 2.

As illustrated in FIG. 1, the CRF correction support system 5 includes the CRF management server 1, the physician's terminal device (a first terminal device) 2, a pharmaceutical company employee's terminal device (a second terminal device) 3, and a communication line 4. The CRF correction support system 5 supports a physician in correcting a CRF that is input.

The CRF management server 1, the physician's terminal device 2, and the pharmaceutical company employee's terminal device 3 may be connected through the communication line 4. For the communication line 4, Local Area Network (LAN), the Internet, public lines or dedicated lines may be used.

The CRF management server 1 includes, as illustrated in FIG. 2, a Central Processing Unit (CPU) 10a, a Random Access Memory (RAM) 10b, a Read Only Memory (ROM) 10c, a hard disk 10d, a Network Interface Card (NIC) 10e, a graphic card 10f, a Universal Serial Bus (USB) interface 10g and various hardware. As the CRF management server 1, a server device is used. A display 1D, a keyboard 1K and a mouse 1M are connected to the CRF management server 1.

A NIC 10e is a device to communicate with the physician's terminal device 2 and the pharmaceutical employee's terminal device 3.

The graphic card 10f performs drawing based on an instruction from the CPU 10a and outputs signals of an image (moving image) to the display 1D.

The USB interface 10g is used to communicate with USB devices. According to the embodiment, the USB interface 10g is particularly used to obtain information that is input by an operator using the keyboard 1K or a mouse 1M.

Programs and data to achieve functions of the following components illustrated in FIG. 3 are installed in the hard disk 10d: such components are a CRF data acquisition unit 101, a CRF export unit 102, a check result data import unit 103, a hash processing unit 104, a correction data acquisition unit 105, a data check unit 106, a re-entry request unit 108, a CRF correction processing unit 107, a CRF data storage unit 121, and a check result data storage unit 122. These programs and data are loaded to the RAM 10b as required and the programs are executed by the CPU 10a. The programs and data to achieve functions illustrated in FIG. 3 are provided by a computer readable storage medium such as a Digital Versatile Disc (DVD)-ROM, a Compact Disc (CD)-ROM, or a USB memory. The storage medium does not include a propagation signal. Moreover, programs and data are provided from a file server, for example, through the Internet.

The physician's terminal device 2 is used by a physician to input or correct a CRF. The physician's terminal device 2 is, as illustrated in FIG. 4, includes a CPU 20a, a RAM 20b, a ROM 20c, a hard disk 20d, a NIC 20e, a graphic card 20f, a liquid crystal display 20g, a keyboard 20h, a pointing device 20i, a DVD drive 20j, a USB interface 20k, and various hardware.

The pharmaceutical company employee's terminal device 3 is used by a pharmaceutical company's employee to check a CRF that is input by a physician. A hardware configuration of the pharmaceutical company employee's terminal device 3 is substantially the same as that of the physician's terminal device 2 illustrated in FIG. 4.

A personal computer or a workstation may be used as the physician's terminal device 2 and the pharmaceutical company employee's terminal device 3.

The CRF management server 1 provides information to the physician's terminal device 2 and the pharmaceutical company employee's terminal device 3 though web pages. Therefore, the CRF management server 1 is provided with a web server function. The CRF management server 1 acquires information from the physician's terminal device 2 and the pharmaceutical company employee's terminal device 3 through a Common Gateway Interface (CGI). Hence, the management server 1 is provided with a CGI function. Web browsers are installed in the physician's terminal device 2 and the pharmaceutical company employee's terminal device 3. Moreover, an editor (spreadsheet software) to edit table data is installed in the pharmaceutical company employee's terminal device 3.

Figure 5:
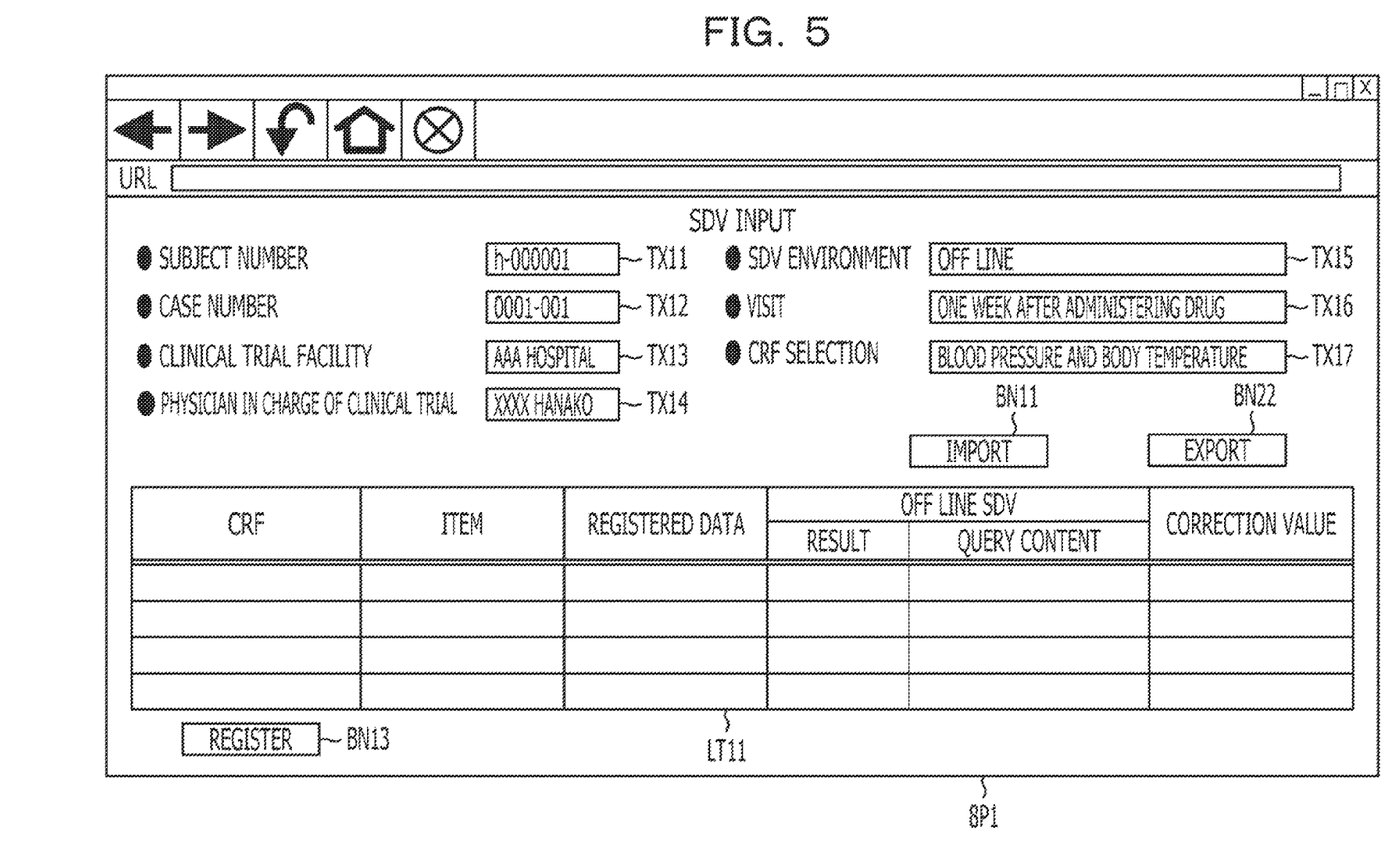
FIG. 5 illustrates an example of a web page for a pharmaceutical company's employee.
Figure 6:
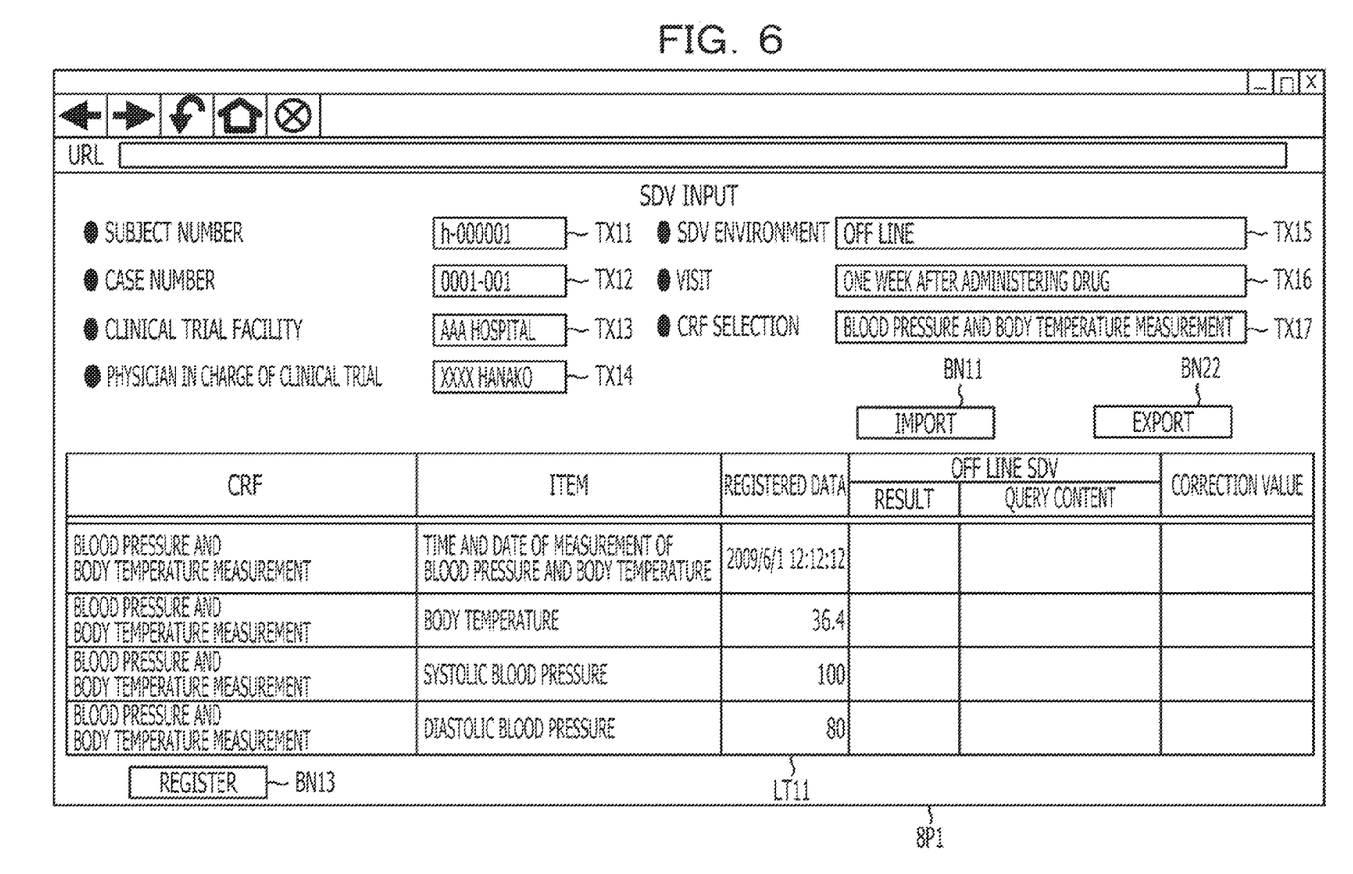
FIG. 6 illustrates an example of a web page for a pharmaceutical company's employee.
Figure 7:
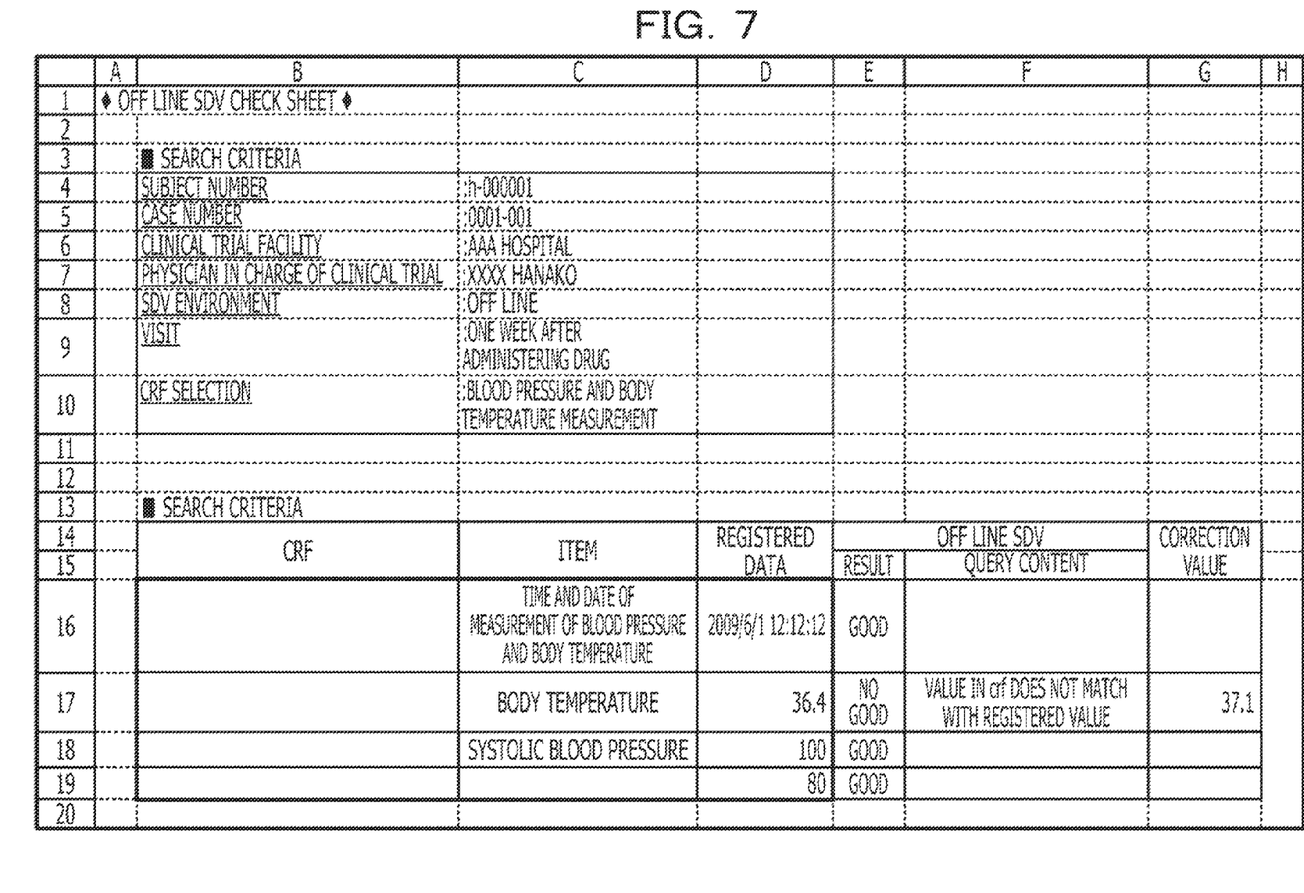
FIG. 7 illustrates an example of a screen for editing table data.
Figure 8:
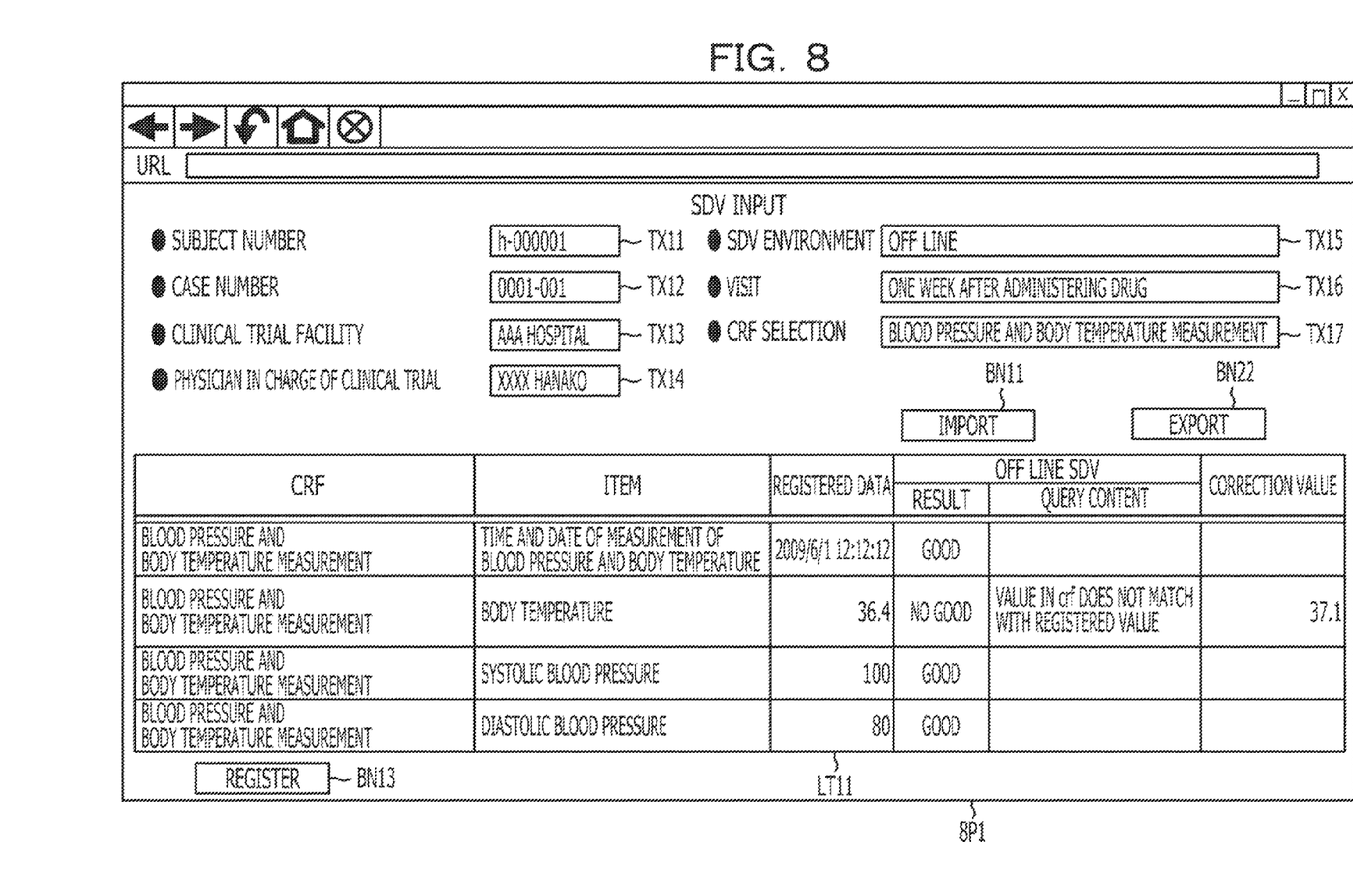
FIG. 8 illustrates an example of a pharmaceutical company employee's web page.
Figure 9:
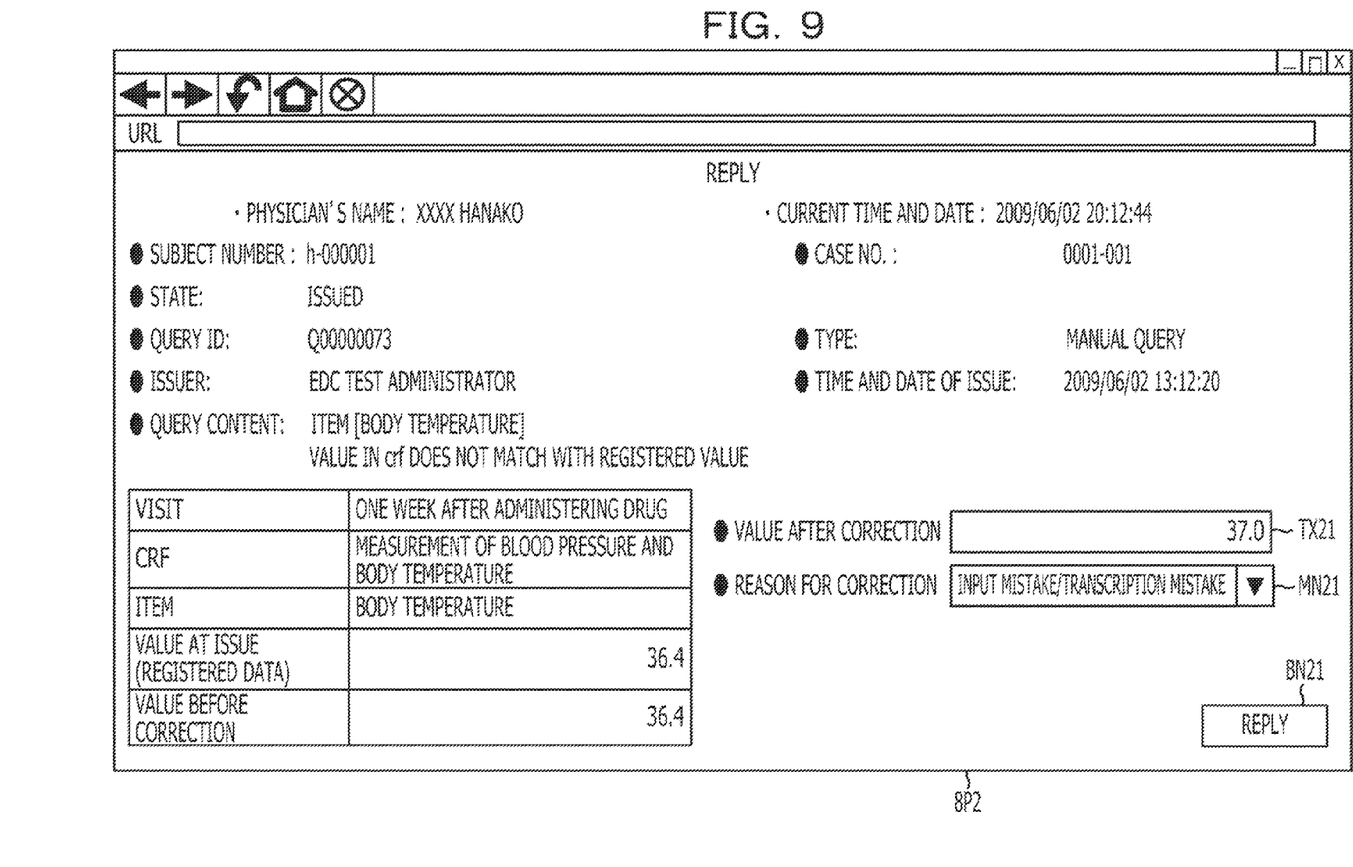
FIG. 9 illustrates an example of a physician's web page.

FIGS. 5 and 6 are examples of a pharmaceutical company employee's web page 8P1. FIG. 7 illustrates an example of a screen for editing table data 71. FIG. 8 illustrates an example of a pharmaceutical company employee's web page 8P1. FIG. 9 illustrates an example of a physician's web page 8P2.

Each of the components of the CRF management server 1, and processing by the physician's terminal device 2 and the pharmaceutical company employee's terminal device 3 illustrated in FIG. 3 will be described.

A physician records results of an examination, an inspection, and a prescription in a medical record whenever the physician examines and inspects a subject of a new drug, and prescribes a drug to the subject. Moreover, the physician creates a CRF based on the medical record. Usually, the content of CRF is all written in the medical record. Thus, the physician creates a CRF by extracting a part of the medical record. A medium for the medical record may be a paper form or an electronic storage medium. However, the CRF is not recorded on paper but recorded in an electronic storage medium.

The physician starts a web browser of the physician's terminal device 2 and makes the physician's terminal device 2 access a web page for inputting a CRF.

The CRF data acquisition unit 101 of the CRF management server 1 performs processing to acquire CRF data as follows.

The CRF data acquisition unit 101 makes the liquid crystal display 20g display a web page for inputting a CRF by transmitting, for example, HyperText Markup Language (HTML) format data.

The physician creates a CRF by inputting data in the web page while referring to the medical record. For example, the physician inputs VISIT of the clinical trial (for example, the day before administering the drug or one week after administering the drug), a CRF type, the physician's identifier, the subject's identifier, and the case's identifier in addition to information of the clinical trial (for example, a measurement value of an inspection, the name and amount of administered drug, symptoms, and a medical history). Hereinafter, a case will be described in which a physician's name is used as an identifier of the physician, a subject number is used as an identifier of the subject, and a case number is used as an identifier of the case.

The physician inputs an upload command after inputting the CRF. The input CRF is transmitted from the physician's terminal device 2 to the CRF management server 1 as CRF data (first information) 70. The CRF data acquisition unit 101 acquires the CRF data 70.

The CRF data 70 is stored in the CRF data storage unit 121. As will be described later, the CRF data 70 may be corrected by the physician.

The CRF export unit 102 performs processing to export the CRF data 70 stored in the CRF data storage unit 121, for example, as will be described below.

The pharmaceutical company's employee visits a facility where a clinical trial is conducted and starts a web browser of the pharmaceutical company employee's terminal device 3 and makes the pharmaceutical company employee's terminal device 3 access a pharmaceutical company employee's web page 8P1 as illustrated in FIG. 5.

The CRF export unit 102 makes the liquid crystal display of the pharmaceutical company employee's terminal device 3 display the pharmaceutical company employee's web page 8P1 by transmitting data of the web page 8P1 to the pharmaceutical company employee's terminal device 3.

Textboxes TX 11 to TX 17, a CRF list LT11 that indicates a CRF, an export button BN11, an import button BN 12, and a register button BN 13 are placed in the pharmaceutical company employee's web page 8P1. No data is input in the Text boxes TX 11 to TX 17 when the web page 8P1 is displayed. Moreover, the CRF list LT11 is a blank other than titles for each field.

The pharmaceutical company's employee inputs a subject number, a case number, and a facility's name where the clinical trial is conducted, and a physician who is responsible for the clinical trial for cases that the employee is in charge of in the text boxes of TX11, TX12, TX13, and TX14 respectively. Furthermore, pharmaceutical company's employee inputs an environment for conducting a Source Document Verification (SDV), timing of the clinical trial, and a CRF type in the text boxes of TX15, TX16, and TX17 respectively.

The input content is transmitted from the pharmaceutical company employee's terminal device 3 to the CRF management server 1. The CRF export unit 102 searches the CRF data storage 121 for the CRF data 70 that indicates the input subject number, the case number, the timing of the clinical trial, and the CRF type, and retrieves the CRF data 70. The CRF export unit 102 generates a table that indicates the CRF and includes a column to input an SDV result based on the retrieved CRF data 70 and transmits data of the pharmaceutical company employee's web page 8P1 on which the generated table is placed to the pharmaceutical company employee's terminal device 3.

The pharmaceutical company employee's terminal device 3 updates the CRF list LT11 based on the received data so that the CRF is indicated as illustrated in FIG. 6, and redisplays the pharmaceutical company employee's web page 8P1. The pharmaceutical company's employee checks whether the CRF indicated in the CRF list LT11 is the CRF to be checked at this time. If the CRF is a correct one, the employee presses the export button BN11.

The pharmaceutical company employee's terminal device 3 stores the content that is input to the text boxes TX11 to TX17 and a table indicated in the CRF list LT11 in a storage medium as data with a format that supports a spreadsheet software. Hereinafter, the data is described as "table data 71."

The pharmaceutical company's employee may store the table data 71 in a hard disk incorporated in the pharmaceutical company employee's terminal device 3, or in a Compact Disc Rewritable (CD-RW) or a USB memory.

Converting the data into a format that supports the spreadsheet software, in other words, generating the table data 71 may be performed by the CRF management server 1 instead by the pharmaceutical company employee's terminal device 3.

The pharmaceutical company's employee starts the spreadsheet software and opens the table data 71 after storing the table data 71 in the storage medium.

As illustrated in FIG. 7, a table format, for example, of a CRF is displayed in the liquid crystal display of the pharmaceutical company employee's terminal device 3. In the table, for each CRF item, a cell is provided for each of "result", "query content", and "correction value." However, no data is input in these cells when the table data 71 is opened.

The pharmaceutical company's employee borrows a medical record on which the CRF is based from the facility that conducts the clinical trial. The pharmaceutical company's employee checks whether any error exists in the CRF by checking the CRF against the medical record.

The pharmaceutical company's employee inputs "GOOD" in the "result" cell for an item of the CRF the content of which matches with that of the medical record.

Meanwhile, the pharmaceutical company's employee inputs "NO GOOD" in the "result" cell for an item the content of which does not match with that of the medical record. Moreover, the pharmaceutical company's employee inputs a content of an inquiry to the physician in the "query content" cell and inputs a value described in the medical record in the "correction value" cell.

Accordingly, an input of a check result is completed. Note that the pharmaceutical company's employee does not input information of a correction value or the information that indicates the correction value in the "query content" cell.

It is desirable that data in cells other than the above-described three types of cells in the table data 71 are locked (protected) so that the pharmaceutical company's employee may not edit the data.

After inputting the check result, the pharmaceutical company's employee inputs an overwrite save command to the pharmaceutical company employee's terminal device 3. The pharmaceutical company employee's terminal device 3 generates a check result data (second information) 72 by adding the input check result, the name of the pharmaceutical company's employee who issues the check result (in other words, an issuer), time and date of the issue to the table data 71.

The pharmaceutical company's employee presses the import button BN12 on the pharmaceutical company employee's web page 8P1. The pharmaceutical company employee's terminal device 3 reads the check result data 72 from the storage medium and updates the CRF list LT11 based on the check result data 72 so that the check result is indicated as illustrated in FIG. 8, and redisplays the pharmaceutical company employee's web page 8P1.

The pharmaceutical company's employee checks whether any error exists in the check result and presses the register button BN 13 if there is no error.

The pharmaceutical company employee's terminal device 3 uploads the check result data 72 to the CRF management server 1.

When the check result data import unit 103 of the CRF management server 1 receives the check result data 72 from the pharmaceutical company employee's terminal device 3, the check result data import unit 103 issues a unique query ID and stores the received check result data 72 in the check result data storage unit 122 in association with the issued query ID. Note that the correction value indicated in the check result data 72 is desired to be converted to a hash value by a hash function. Conversion to the hash value may be executed by the pharmaceutical company employee's terminal device 3 or by the CRF management server 1. According to the embodiment, the hash processing unit 104 converts the data into a hash value. The check result data 72 after the conversion is stored in the check result data storage unit 122.

The physician who is responsible for the clinical trial corrects an error entry in the CRF if there is any error entry after the pharmaceutical company's employee checks the CRF.

The correction data acquisition unit 105 executes processing to acquire a content of a correction made by the physician, for example, as follows.

The physician starts a web browser of the physician's terminal device 2 and makes the physician's terminal device 2 access a web page to correct the CRF that is provided by the CRF management server 1. The physician inputs own name.

The correction data acquisition unit 105 searches the check result data storage unit 122 for the check result data 72 that indicates the physician in charge of the clinical trial whose name corresponds to the name of the physician that is input. The correction data acquisition unit 105 transmits data based on the check result data 72 to display a physician's web page 8P2 as illustrated in FIG. 9 to the physician's terminal device 2. As a result, the physician's web page 8P2 is displayed in the liquid crystal display 20g of the physician's terminal device 2.

In the physician's web page 8P2, the subject number, the case number, the issuer, the date and time of issue, an error entry item that the issuer found in the original CRF, and the value (registered data), the content of query for the error entry, timing of the clinical trial (VISIT), and a CRF type. However, the correction value that is input by the pharmaceutical company's employee is not described.

Moreover, a text box TX21, a pull down menu MN21, and a reply button BN21 are placed in the physician's web page 8P2. When the physician's web page 8P2 is displayed in the liquid crystal display 20g, the text box TX21 is a blank and no item is selected in the pull down menu MN21.

The physician confirms the correct value by obtaining the medical record of the subject with the subject number indicated in the physician's web page 8P2 and inputs the correct value in the text box TX21. Furthermore, the physician clicks the pull down menu MN21 to display a list and selects a reason for changing the previously input error entry into the correct value and presses the reply button BN21.

The physician's terminal device 2 transmits correction data 73 that indicates the content that is input in the text box TX21 and selected in the pull down menu MN21 to the CRF management server 1. If there are error entries in a plurality of items, text boxes for each of the items are displayed in the physician's web page 8P2. The physician corrects errors for each of the items.

The correction data acquisition unit 105 of the CRF management server 1 acquires the correction data (third information) 73 by receiving the correction data 73 from the physician's terminal device 2.

Accordingly, the CRF management server 1 acquires the check result data 72 that indicates the check result by the pharmaceutical company's employee and the correction data 73 that indicates a value corrected by the physician for one CRF.

The data check unit 106 checks values in items that are common to the check result data 72 and the correction data 73 acquired for the one CRF. For example, a value for body temperature indicated in the check result data 72 is checked against a value for body temperature indicated in the correction data 73.

However, as described above, the value (correction value) indicated in the check result data 72 is converted into a hash value by the hash processing unit 104. Accordingly, the data check unit 106 converts the value indicated in the correction data 73 into a hash value by the hash function used by the hash processing unit 104. The two hash values are checked against each other.

As a result of the check by the data check unit 106, if values in items that are common to the check result data 72 and the correction data 73 do not match, the re-entry request unit 108 transmits a message requesting re-entry of a correct value by checking the medical record again to the physician's terminal device 2. For example, a message such as "the correction value does not match with the value in the original data checked at SDV" is transmitted. The message is displayed in the liquid crystal display 20g of the physician's terminal device 2.

If the two values match, the CRF correction processing unit 107 searches the CRF data storage unit 121 for a CRF data 70 of the CRF that is corrected by the physician. The CRF correction processing unit 107 rewrites a value of an item in the CRF data 70 to a value corrected by the physician (a value indicated in the correction data 73).

There may be a case in which a value when a physician creates a CRF is correct and a result of SVD by a pharmaceutical company's employee is incorrect. Thus, the physician's terminal device 2 displays a dialogue box for selecting whether to correct the value or not. The physician returns a reply indicating the result of the SDV is incorrect to the CRF management server 1 by selecting not to correct the value. The CRF management server 1 does not correct data of an item that the pharmaceutical company's employee erroneously determines the error entry. Alternatively, the CRF management server 1 updates the CRF data 70 by using the value corrected by the physician based on an instruction from the physician.

Accordingly, the CRF data 70 is checked by the pharmaceutical company's employee, and the physician and the content is fixed. The fixed CRF data 70 is locked (protected) so as not to be rewritten.

Figure 10:
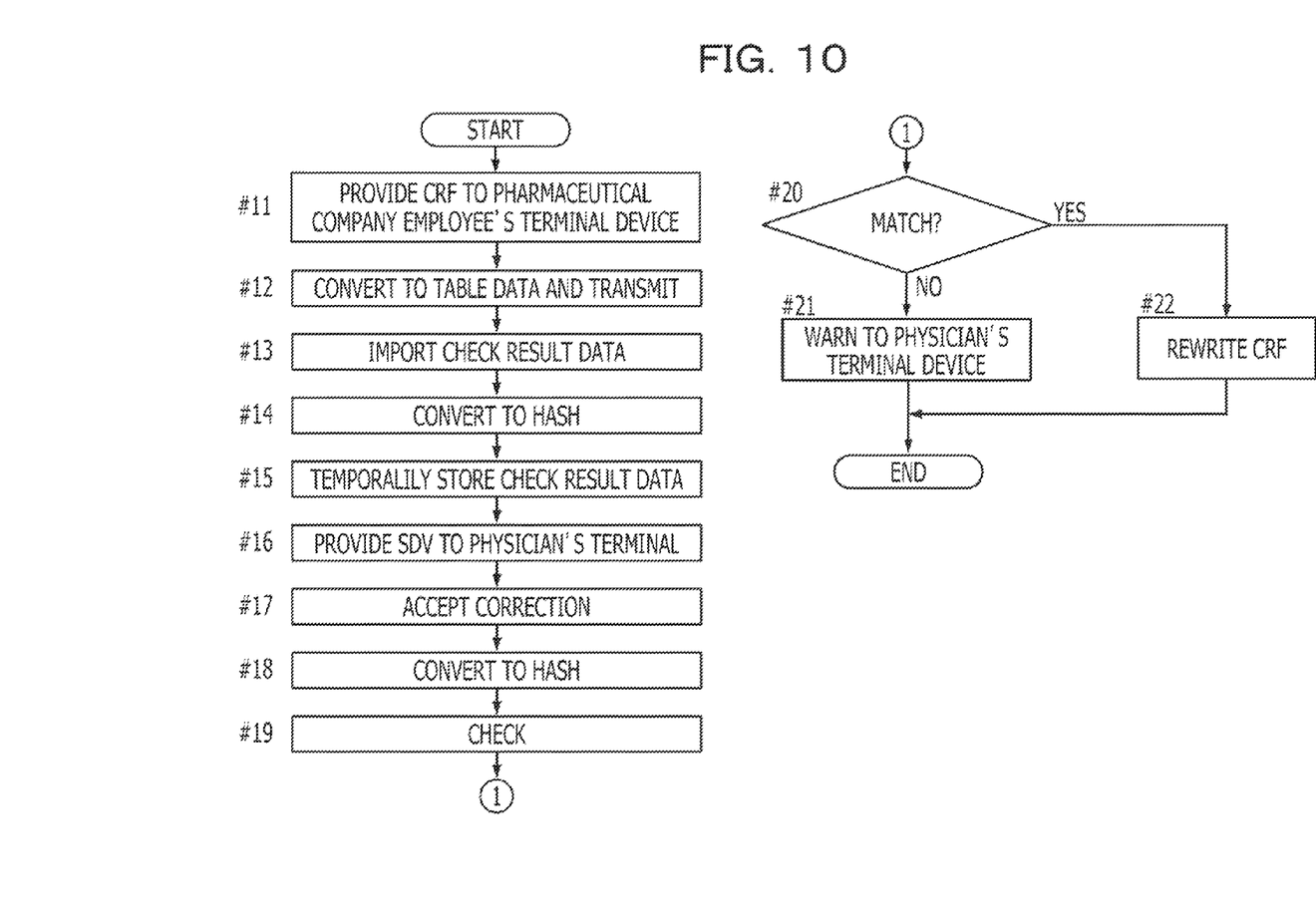
FIG. 10 is a flow chart illustrating an overall processing flow of the CRF management server.
Figure 11:
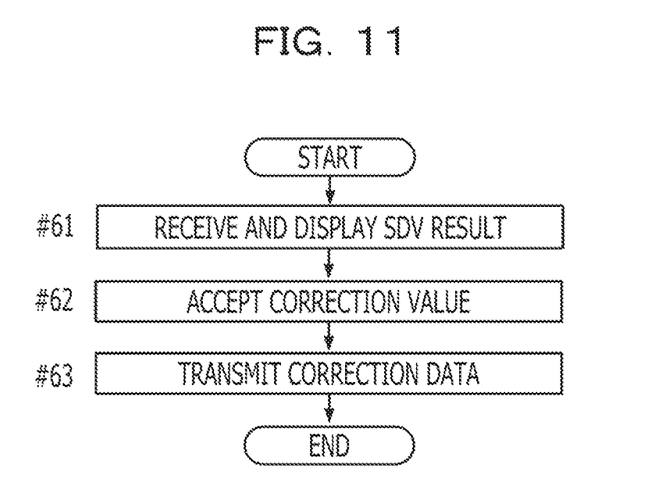
FIG. 11 is a flow chart illustrating an overall processing flow of a physician's terminal device.
Figure 12:
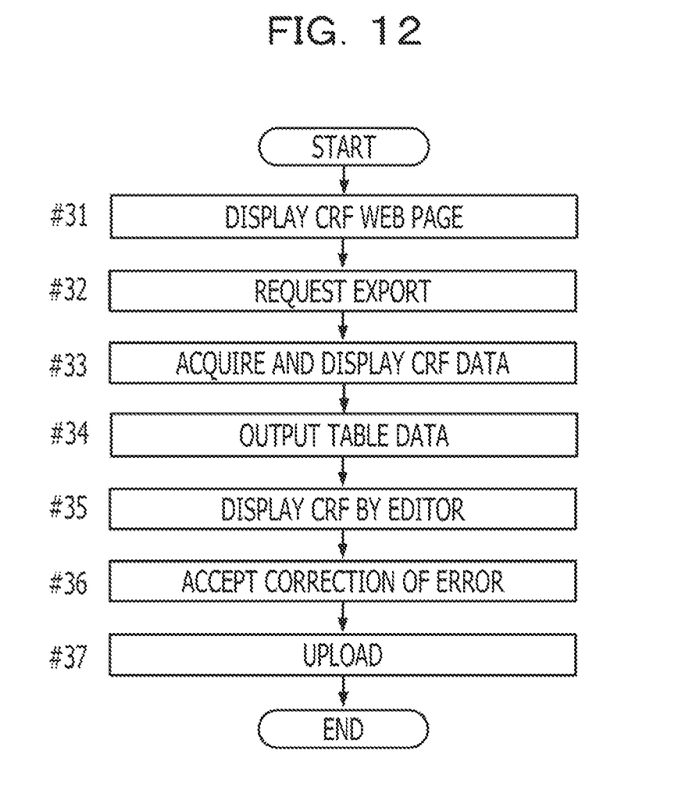
FIG. 12 is a flow chart illustrating an overall processing flow of a pharmaceutical company employee's terminal device.

FIG. 10 is a flow chart illustrating an overall processing flow of the CRF management server 1. FIG. 11 is a flow chart illustrating an overall processing flow of the physician's terminal device 2. FIG. 12 is a flow chart illustrating an overall processing flow of the pharmaceutical company employee's terminal device 3.

Overall processing flows of the CRF management server 1, physician's terminal device 2, and the pharmaceutical company employee's terminal device 3 will be described by referring to flow charts illustrated in FIGS. 10 to 12.

After the physician inputs the CRF, the pharmaceutical company's employee makes the pharmaceutical company employee's terminal device 3 access the CRF management server 1. The pharmaceutical company employee's terminal device 3 displays the pharmaceutical company employee's web page 8P1 as illustrated in FIG. 5 (#31 of FIG. 12).

The pharmaceutical company's employee inputs attributes of the CRF (for example, the subject number, the case number, and the physician's name) that the employee should check in the pharmaceutical company employee's web page 8P1. The pharmaceutical company employee's terminal device 3 requests the CRF management server 1 to export the CRF with the attributes that are input (#32). The CRF management server 1 transmits data of the pharmaceutical company employee's web page 8P1 in which the CRF is placed to the pharmaceutical company employee's terminal device 3 (#11 of FIG. 10). The pharmaceutical company employee's terminal device 3 acquires the data and redisplays the pharmaceutical company employee's web page 8P1 as illustrated in FIG. 6 (#33).

When the pharmaceutical company's employee presses the export button BN11, the pharmaceutical company employee's terminal device 3 outputs the table data 71 to the storage device (#34). The table data 71 may be generated by the CRF management server 1 or by the pharmaceutical company employee's terminal device 3. The flow chart of FIG. 10 illustrates the former case (refer to #12).

The pharmaceutical company employee's terminal device 3 opens the table data 71 by the spreadsheet software and displays the CRF as illustrated in FIG. 7 (#35). The pharmaceutical company's employee checks if there is any error entry in the CRF while referring to the medical record on which the CRF is based. The pharmaceutical company's employee inputs the check result. In other words, if any correction is needed, the pharmaceutical company's employee inputs a correction value in association with an item that needs to be corrected.

The pharmaceutical company employee's terminal device 3 accepts the input content (#36) and uploads the check result data 72 that indicates the accepted content to the CRF management server 1 (#37). When the CRF management server 1 acquires (imports) the check result data 72 from the pharmaceutical company employee's terminal device 3 (#13), the CRF management server 1 converts the correction value data into a hash value and stores the check result data 72 (#14 and #15). Accordingly, proving to the third party that the correction data itself is not leaked to the physician through the CRF management server 1 may be easier because the correction value data of the check result data 72 stored in the CRF management server 1 is converted into the hash value and the correction value data itself is not stored in the CRF management server 1.

The CRF management server 1 makes the physician's terminal device 2 display the physician's web page 8P2 (#16 and #61 of FIG. 11) for correcting the CRF by the physician. As illustrated in FIG. 9, a position where an error entry is caused in the CRF, in other words, the item is indicated in the physician's web page 8P2, but the correction value that is input for the error entry by the pharmaceutical company's employee is not indicated. The physician inputs a correction value for the error entry while referring to the displayed query content and a medical record on which the CRF is based.

The physician's terminal device 2 accepts the correction value (#62) and transmits the correction data 73 to the CRF management server 1 (#63).

The CRF management server 1 converts the correction value into a hash value (#18) when the CRF management server 1 receives the correction data 73 from the physician's terminal device 2 (#17). The CRF management server 1 checks the hash value against the hash value converted at Operation #14 (#19).

If the two values do not match (No at #20), the CRF management server 1 warns the physician by transmitting a message requesting the physician to re-entry of the correct value (#21). The CRF management server 1 waits that correction data 73 is transmitted again.

If the two values match (Yes at #20), the CRF management server 1 rewrites the error entry in the CRF data 70 to the correction value that is input by the physician (#22).

According to the embodiment, the physician may accurately correct a CRF without exceeding a conventional burden.

According to the embodiment, the correction value is converted into a hash value by using a hash function. However, the correction value may be converted by using one-way (irreversible) conversion logic. Reversible conversion logic (for example, secret key cryptography) may be used as long as robustness with a certain level is achieved.

According to the embodiment, as an example, correcting the CRF is described. However, the present disclosure may be applied to correct another type of information. Particularly, the present disclosure may be applied to a correction that is typically allowed to a person with a certain authority.

All of or a part of configurations of the CRF correction support system 5, the CRF management server 1, the physician's terminal device 2, and the pharmaceutical company employee's terminal device 3, processing contents, processing order, and configuration of data may be changed as appropriate along with the spirit of the present disclosure.

For example, the above-described operations #18 to #21 may be executed by the physician's terminal device 2. In this case, the CRF management server 1 embeds the hash data obtained by converting the above described correction value in association with the item indicated as an error entry in the physician's web page 8P2 (refer to FIG. 9) that is transmitted from the CRF management server 1 to the physician's terminal device 2 at operation #16. Moreover, the CRF management server 1 embeds software modules that run over the physician's terminal device 2 to perform processing of converting the correction value input by the physician into the second hash data (#18) and processing of displaying a warning if needed after checking the above-described hash data embedded in the physician's web page 8P2 against the above-described second hash data (#19 to #21). The software modules may be implemented, for example, by using the Java (registered trademark) Script that may be executed over the web browser. The software modules may be provided by a computer readable storage medium such as a DVD-ROM, a CD-ROM, or a USB memory. The storage medium does not include a propagation signal. The software modules are provided by a file server through the Internet.

According to the embodiment, the physician's terminal device 2 and the pharmaceutical company employee's terminal device 3 use web browsers in order to use functions of the CRF management server 1. However, dedicated software programs may be used instead. In this case, a program that sequentially executes each of the processing illustrated in FIGS. 11 and 12 may be prepared. The program may be provided by a computer readable storage medium such as a DVD-ROM, a CD-ROM, or a USB memory. The storage medium does not include a propagation signal. The program is provided by a file server through the Internet.

According to the embodiment, information such as a CRF may be corrected more accurately without increasing a burden on an operator who makes a correction.

Example and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention have been described in detail, it should be understood that the various changes, substitutions, and alterations could be made hereto without departing from the spirit and scope of the invention.

What is claimed is:

1. An information correction support system comprising:
a first processor configured to:
provide first information that is input by a first user to a second user; and
accept an error entry position in the first information, and second information that is correct information corresponding to the error entry position that are input by the second user;
a second processor configured to:
provide the error entry position to the first user without providing the second information; and
accept third information that is correction information corresponding to the error entry position input by the first user without referring to the second information; and
a third processor configured to:
determine whether the third information is correctly input information based on the second information; and
warn the first user when the third information is determined to be incorrectly input information.

2. The information correction support system according to claim 1,
wherein the third processor is further configured to determine whether the third information is correctly input information based on the second information.

3. The information correction support system according to claim 2, wherein the third processor is further configured to:
convert the second information into second conversion information by using a one-way conversion logic and stores the second conversion information; and
determine whether the third information is correctly input information by checking the second conversion information obtained by converting the second information against third conversion information obtained by converting the third information by using the one-way conversion logic.

4. The information correction support system according to claim 3, wherein the one-way conversion logic is a hash function.

5. The information correction support system according to claim 1, wherein the second processor displays a dialogue box for selecting whether to correct the third information or not when the third information is determined to be incorrectly input information.

6. An information correction support server comprising:
a memory, and
a processor coupled to the memory and configured to:
transmit first information that is input by a first user to a second terminal device operated by a second user;
receive an error entry position in the first information, and second information that is correct information corresponding to the error entry position that are input by the second user from the second terminal device;
transmit the error entry position to a first terminal device operated by the first user without transmitting the second information;
receive third information that is correction information corresponding to the error entry position input by the first user without referring to the second information from the first terminal device;
determine whether the third information is correctly input information based on the second information; and
transmit a warning message to the first terminal device when the third information is determined to be incorrectly input information.

7. A method to support correcting input information by a computer, the method comprising:
providing first information that is input by a first user to a second user;
accepting an error entry position in the first information, and second information that is correct information corresponding to the error entry position that are input by the second user;
providing the error entry position to the first user without providing the second information;
accepting third information that is correction information corresponding to the error entry position input by the first user without referring to the second information;
determining whether the third information is correctly input information based on the second information; and
warning the first user when the third information is determined to be incorrectly input information.

8. The method to support correcting input information by a computer according to claim 7, further comprising:
converting the second information into second conversion information by using a one-way conversion logic and storing the second conversion information; and
determining whether the third information is correctly input information by checking the second conversion information obtained by converting the second information against third conversion information obtained by converting the third information by using the one-way conversion logic,
wherein the one-way conversion logic is a hash function.

9. The method to support correcting input information by a computer according to claim 7, further comprising:
displaying a dialogue box for selecting whether to correct the third information or not when the third information is determined to be incorrectly input information.

10. A non-transitory computer-readable recording medium that stores a program for causing a computer to execute an information correction support process of correcting first information that is input by a first user, the process comprising:
transmitting the first information to a second terminal device operated by a second user;
receiving an error entry position in the first information, and second information that is correct information corresponding to the error entry position that are input by the second user from the second terminal device;
transmitting the error entry position received from the second terminal device to a first terminal device operated by the first user without transmitting the second information received;
receiving third information that is correction information corresponding to the error entry position input by the first user without referring to the second information from the first terminal device; and
determining whether the third information received from the first terminal device is correctly input information based on the second information received from the second terminal device, wherein warning processing is executed in which a warning message is transmitted to the first terminal device when the third information is determined to be incorrectly input information.

* * * * *